United States Patent
Gittard et al.

(10) Patent No.: US 10,328,258 B2
(45) Date of Patent: Jun. 25, 2019

(54) ELECTROTHERAPEUTIC SYSTEMS, DEVICES, AND METHODS

(71) Applicant: Cook Medical Technologies LLC, Bloomington, IN (US)

(72) Inventors: Shaun Davis Gittard, Winston-Salem, NC (US); John Crowder Sigmon, Jr., Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 15/254,305

(22) Filed: Sep. 1, 2016

(65) Prior Publication Data

US 2017/0056652 A1 Mar. 2, 2017

Related U.S. Application Data

(60) Provisional application No. 62/213,356, filed on Sep. 2, 2015.

(51) Int. Cl.
*A61N 1/36* (2006.01)
*A61N 1/05* (2006.01)
*A61N 1/375* (2006.01)

(52) U.S. Cl.
CPC ....... *A61N 1/36007* (2013.01); *A61N 1/0507* (2013.01); *A61N 1/36014* (2013.01);
(Continued)

(58) Field of Classification Search
CPC ............ A61N 1/36007; A61N 1/36014; A61N 1/0507; A61N 1/3752; A61N 1/36157;
(Continued)

(56) References Cited

U.S. PATENT DOCUMENTS

| | | | |
|---|---|---|---|
| 5,495,851 A * | 3/1996 | Dill | A61B 8/12 600/439 |
| 6,687,538 B1 * | 2/2004 | Hrdlicka | A61N 1/36014 600/547 |

(Continued)

FOREIGN PATENT DOCUMENTS

| | | |
|---|---|---|
| JP | 1990-006057 | 1/1990 |
| JP | 2004-532700 A | 10/2004 |

(Continued)

OTHER PUBLICATIONS

Ted L. Tewfik et al., "Vagus Nerve Anatomy", http://emedicine.medscape.com/article/1875813-overview, Aug. 17, 2015, 6 pages.

(Continued)

*Primary Examiner* — Rex R Holmes
(74) *Attorney, Agent, or Firm* — Brinks Gilson & Lione

(57) ABSTRACT

Electrotherapeutic systems, devices, and methods are described. In one embodiment, a portion of a hepatic branch of a vagus nerve in a liver is stimulated with a lead implanted in the liver. In another embodiment, a stimulation member is delivered to a location in the gastrointestinal tract and implanted in a target area endoscopically and under ultrasound visualization. In another embodiment, a stimulation device is magnetically coupled to a stimulation member in order to electrically couple stimulation generation circuitry with a lead implanted in a target area.

16 Claims, 10 Drawing Sheets

(52) U.S. Cl.
CPC ..... *A61N 1/36017* (2013.01); *A61N 1/36034* (2017.08); *A61N 1/36157* (2013.01); *A61N 1/36171* (2013.01); *A61N 1/36175* (2013.01); *A61N 1/0509* (2013.01); *A61N 1/36053* (2013.01); *A61N 1/3752* (2013.01)

(58) Field of Classification Search
CPC .............. A61N 1/36171; A61N 1/0509; A61N 1/36053; A61N 1/36175
See application file for complete search history.

(56) References Cited

U.S. PATENT DOCUMENTS

| | | | |
|---|---|---|---|
| 8,026,651 | B2 | 9/2011 | Wakabayashi et al. |
| 2002/0165589 | A1 | 11/2002 | Imran et al. |
| 2007/0021736 | A1* | 1/2007 | Johnson ............. A61B 17/0401 606/1 |
| 2011/0275891 | A1* | 11/2011 | Shemi ................. A61M 31/007 600/104 |
| 2013/0178910 | A1* | 7/2013 | Azamian .......... A61B 17/00234 607/33 |
| 2014/0243593 | A1 | 8/2014 | Goode et al. |
| 2015/0224311 | A1 | 8/2015 | Yun et al. |
| 2015/0297885 | A1* | 10/2015 | Goode ................ A61N 1/0509 606/129 |

FOREIGN PATENT DOCUMENTS

| | | |
|---|---|---|
| JP | 2006-515999 A | 6/2006 |
| JP | 2015-502820 A | 1/2015 |
| WO | WO 2004/043218 | 5/2004 |
| WO | WO 2008/070808 | 6/2008 |
| WO | WO 2013/086461 | 6/2013 |
| WO | WO 2014/097034 | 6/2014 |

OTHER PUBLICATIONS

S. Andrei Ostric, MD, Essentials of the gut-brain connection: Vagus nerve anatomy, Feb. 8, 2013, http://www.midwestprs.com/essentials-of-the-gut-brain-connection-vagus-nerve-anatomy.

International Search Report and Written Opinion for corresponding application No. PCT/US2016/049842 dated Jan. 2, 2017.

Examination Report for corresponding Australian Application No. 2016317840 dated Jan. 18, 2019 (5 pgs).

Japanese Office Action, including translation, dated Mar. 12, 2019 for corresponding application No. JP 2018-511222 dated Mar. 12, 2019 (11 pages).

* cited by examiner

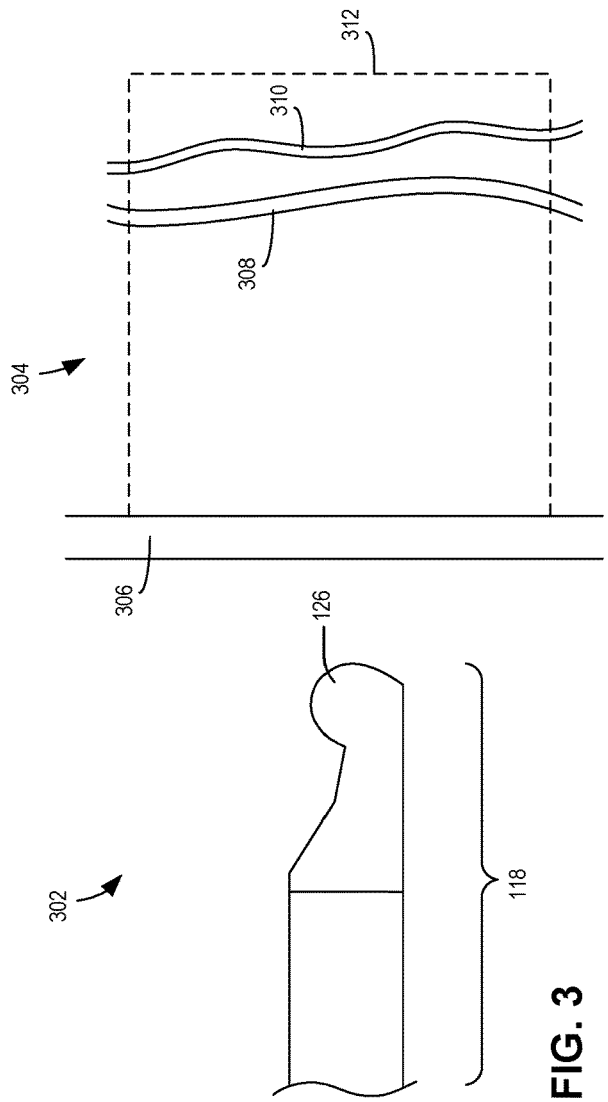
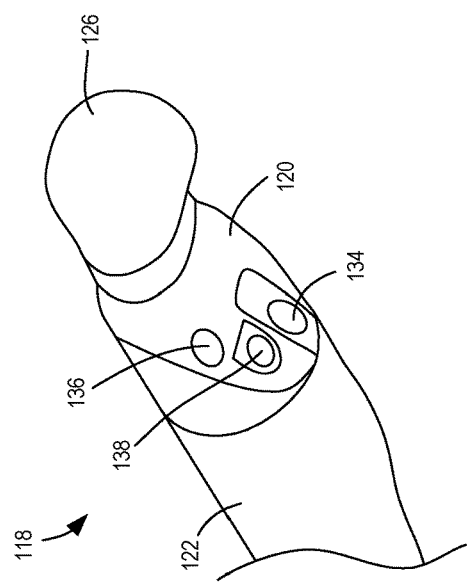
FIG. 2
FIG. 3

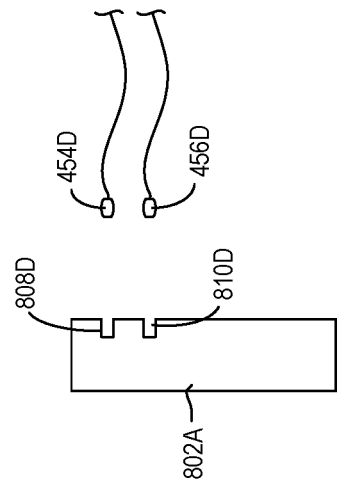
FIG. 8B
FIG. 8C
FIG. 8A

ELECTROTHERAPEUTIC SYSTEMS, DEVICES, AND METHODS

CROSS-REFERENCE TO RELATED APPLICATIONS

This application claims the benefit of U.S. Provisional Application No. 62/213,356, filed Sep. 2, 2015. The contents of U.S. Provisional Application No. 62/213,356 are hereby incorporated by reference in their entirety.

TECHNICAL FIELD

The present invention relates generally to medical devices and more particular to electrotherapeutic medical systems, devices, and methods.

BACKGROUND

Electrical stimulation therapy or electrotherapy may be used to treat various health disorders, such as obesity and gastroparesis, by applying electrical signals having specific waveforms through a pair of stimulation electrodes. Some types of electrotherapy involve placing electrodes into a muscularis layer of a gastrointestinal wall or on a surface of the liver. To supply the electrotherapeutic signals, a stimulator or pacer may be positioned subcutaneously. The stimulation electrodes may be implanted in a patient through invasive or open surgery, which may involve making an incision into the patient's skin and gaining access into his/her abdominal cavity. Invasive or open surgical procedures have drawbacks compared to minimally invasive or endoscopic ones. Such drawbacks may include higher complication rates (including higher risks of infection) and longer recovery times. Due to these drawbacks, minimally invasive or endoscopic therapeutic procedures may be desirable, including minimally invasive or endoscopic procedures for implanting stimulation electrodes in a patient and/or for delivering a stimulation device and connecting the stimulation device to stimulation electrodes. Furthermore, although applying electrodes to a surface of a patient's liver may provide some beneficial electrotherapeutic effects, it may be desirable to specifically target certain nerves within the liver for stimulation, and implant stimulation electrodes inside the liver at or near these targeted nerves.

BRIEF SUMMARY

The present description describes electrotherapeutic medical devices, systems, and methods for: stimulating a patient's hepatic branch of the vagus nerve; positioning stimulation electrodes or leads using endoscopic ultrasound; and coupling a stimulation device to stimulation leads inside a patient using magnetic connectors. In one embodiment, a method of stimulation in a patient is performed. The method includes: endoscopically delivering a distal portion of a delivery and deployment device to a location of a gastrointestinal tract of the patient; using the delivery and deployment device, distally advancing the lead of the stimulation member from the gastrointestinal tract location to a target area within a patient, wherein the lead is implanted in the target area after being moved to the target area; and activating an ultrasound transducer to generate an ultrasound image of at least one of the lead being moved from the gastrointestinal tract location to the target area or the lead implanted in the target area.

In some embodiments, the method includes: advancing a distal tip of a hollow needle of the delivery and deployment device from the gastrointestinal tract location into the target area, wherein distally advancing the lead of the stimulation member comprises distally advancing the lead from within a needle lumen of the hollow needle past the distal tip of the needle when the distal tip is positioned in the target area.

In some embodiments, advancing the distal tip of the hollow needle includes advancing the distal tip of the hollow needle from the gastrointestinal tract location into the target area while the ultrasound transducer is activated.

In some embodiments, the ultrasound transducer is coupled to a distal portion of an endoscopic ultrasound device and the method further includes: advancing the distal portion of the endoscopic ultrasound device to the gastrointestinal tract location, wherein endoscopically delivering the distal portion of the delivery and deployment device to the gastrointestinal tract location comprises advancing the delivery and deployment device through a working channel of the endoscopic ultrasound device.

In some embodiments, the method further includes: electrically stimulating the target area with the lead of the stimulation area with the lead of the stimulation member implanted in the target area.

The some embodiments, the target area is in a liver of the patient, and wherein electrically stimulating the target area comprises electrically stimulating a portion of a nerve in the liver.

In some embodiments, the portion of the nerve comprises the hepatic branch of the vagus nerve.

In some embodiments, the target area in the liver is defined relative to a portal vein in the liver of the patient, and the method further includes transmitting, with the ultrasound transducer, ultrasound toward the portal vein to generate the ultrasound image.

In some embodiments, electrically stimulating the hepatic branch includes electrically stimulating the hepatic branch with pulsed electrical stimulation signals.

In some embodiments, the pulsed signals have at least one of: a pulse frequency of 40 Hertz (Hz) or less, a pulse width of 0.3 milliseconds (ms), a power component of 13 Watts or less, or a maximum amplitude of a current component of 4 milliAmps (mA) or less.

In some embodiments, the target area is in or on a gallbladder of the patient.

In some embodiments, the method further includes: coupling a stimulation device connector of a stimulation device to a stimulation member connector of the stimulation member, wherein stimulation generation circuitry of the stimulation device is electrically coupled to the lead of the stimulation member when the stimulation device connector is coupled to the stimulation member connector.

In some embodiments, coupling the stimulation device connector to the stimulation member connector includes magnetically coupling the stimulation device connector to the stimulation member connector.

In some embodiments, coupling the stimulation device connector to the stimulation member connector comprises mechanically coupling the stimulation device connector to the stimulation member connector.

In some embodiments, the method further includes: delivering the stimulation device to a location in a gastrointestinal tract of the patient with the stimulation device connector uncoupled with the stimulation member connector, wherein coupling the stimulation device connector to the stimulation member connector includes coupling the stimulation device connector to the stimulation member connector at the gastrointestinal tract location.

In some embodiments, coupling the stimulation device connector to the stimulation member includes coupling the stimulation device connector to the stimulation member connector outside of the patient, and the method further includes: delivering the stimulation device to a location in a gastrointestinal tract of the patient with the stimulation device connector coupled to the stimulation member connector.

In some embodiments, the stimulation member includes a coupling wire that couples the lead to the stimulation member connector, and the method further includes: recoiling, with a recoil device, an access portion of the coupling wire as the stimulation device is delivered to the gastrointestinal tract location.

In some embodiments, the method further includes: delivering the stimulation device to a location in a gastrointestinal tract of the patient by moving the stimulation device over a wire guide.

In some embodiments, the method further includes: forming a removable connection between the stimulation device connector and the stimulation member connector when coupling the stimulation device connector to the stimulation member connector.

In a second embodiment, a stimulation device includes stimulation generation circuitry and a stimulation device connector. The stimulation generation circuitry is configured to generate electrical stimulation signals for electrotherapeutic stimulation of an anatomical area within a patient. The stimulation device connector is configured for removable connection with a stimulation member connector of a stimulation member.

In some embodiments, the stimulation device connector includes a magnetic stimulation device connector configured to magnetically couple with the stimulation member connector to form the removable connection.

In some embodiments, the stimulation member connector is configured to mechanically couple with the stimulation member connector to form the removable connection.

In some embodiments, the electrical stimulation signals are pulsed electrical stimulation signals.

In some embodiments, the pulsed signals have a pulse frequency of 40 Hertz (Hz) or less.

In some embodiments, the pulse frequency is 14 Hz.

In some embodiments, the pulsed signals have a pulse width of 0.3 milliseconds (ms).

In some embodiments, a power component of the pulsed signals is 13 Watts or less.

In some embodiments, the power component is 5 Watts.

In some embodiments, a current component of the pulsed signals has a maximum amplitude of 4 milliAmps (mA) or less.

In some embodiments, the stimulation device includes a housing coated with a silicone-based or a parylene-based coating.

In some embodiments, the stimulation device includes a wire guide engaging portion sized to engage with and be movably disposed over a wire guide.

In a third embodiment, an electrotherapeutic system includes a stimulation device and a stimulation member. The stimulation device includes stimulation generation circuitry configured to generate electrical stimulation signals for electrotherapeutic stimulation of an anatomical area within a patient, and a stimulation device connector configured for removable connection. The stimulation member includes a lead configured for implantation in the anatomical area, and a stimulation member connector configured for removable connection with the stimulation device connector. When the stimulation device connector is connected to the stimulation member connector, the stimulation generation circuitry is electrically coupled to the lead.

In some embodiments, the stimulation device connector and the stimulation member connector are configured to be magnetically coupled to each other to form the removable connection.

In some embodiments, the stimulation device connector and the stimulation member connector are configured to be mechanically coupled to each other to for the removable connection.

In some embodiments, the stimulation member includes a coupling wire that couples the lead with the stimulation member connector, wherein a length of the coupling wire is sized so that when the lead is implanted in the anatomical area, the stimulation member connector is disposed in a location in the gastrointestinal tract.

In some embodiments, the stimulation member includes a coupling wire that couples the lead with the stimulation member connector, wherein a length of the coupling wire is sized so that when the lead is implanted in the anatomical area, the stimulation member connector is disposed in a location outside of the patient.

In some embodiments, the electrotherapeutic system includes a recoil device configured to pull in an access portion of the coupling wire for when the stimulation device is positioned in a final location in the patient.

In a fourth embodiment, a method of electrically stimulating a hepatic branch of a vagus nerve of a patient is performed. The method includes: identifying a target area within a liver that is defined by a portal vein in the liver of the patient; implanting a lead of a stimulation member in the target area of the liver; and electrically stimulating the hepatic branch of the vagus nerve with the lead of the stimulation member implanted in the target area.

In some embodiments, the method further includes transmitting, with an ultrasound transducer, ultrasound toward the portal vein in the liver; and generating, with an ultrasound imaging apparatus, an ultrasound image based on the ultrasound transmitted toward the portal vein, wherein the target area is identified based on the generated ultrasound image.

In some embodiments, the method further includes: endoscopically delivering a distal portion of a delivery and deployment device to a location of a gastrointestinal tract of the patient; and using the delivery and deployment device, distally advancing the lead of the stimulation member from the gastrointestinal tract location to the target area, wherein the lead is implanted in the target area after being moved to the target area.

In some embodiments, the method further includes: activating an ultrasound transducer to generate an ultrasound image of at least one of the lead being moved from the gastrointestinal tract location to the target area or the lead implanted in the target area.

In some embodiments, an ultrasound transducer is coupled to a distal portion of an endoscopic ultrasound device, and the method further includes: advancing the distal portion of the endoscopic ultrasound device to the gastrointestinal tract location, wherein endoscopically delivering the distal portion of the delivery and deployment device to the gastrointestinal tract location comprises advancing the delivery and deployment device through a working channel of the endoscopic ultrasound device.

In some embodiments, electrically stimulating the hepatic branch includes electrically stimulating the hepatic branch with pulsed electrical stimulation signals.

In some embodiments, the pulsed signals have a pulse frequency of 40 Hertz (Hz) or less.

In some embodiments, the pulse frequency is 14 Hz.

In some embodiments, the pulsed signals have a pulse width of 0.3 milliseconds (ms).

In some embodiments, a power component of the pulsed signals is 13 Watts or less.

In some embodiments, the power component is 5 Watts.

In some embodiments, a current component of the pulsed signals has a maximum amplitude of 4 milliAmps (mA) or less.

In some embodiments, a boundary of the target area is defined by a distance of ten millimeters from a portion of the portal vein.

In a fifth embodiment, a method of implanting a lead of a stimulation member in target area of a patient is performed. The method includes: endoscopically delivering a distal portion of a delivery and deployment device to a location of a gastrointestinal tract of the patient; using the delivery and deployment device, distally advancing the lead of the stimulation member from the gastrointestinal tract location to the target area, wherein the lead is implanted in the target area after being moved to the target area; and activating an ultrasound transducer to generate an ultrasound image of at least one of the lead being moved from the gastrointestinal tract location to the target area or the lead implanted in the target area.

In some embodiments, the method further includes: advancing a distal tip of a hollow needle of the delivery and deployment device from the gastrointestinal tract location into the target area, wherein distally advancing the lead of the stimulation member comprises distally advancing the lead from within a needle lumen of the hollow needle past the distal tip of the needle when the distal tip is positioned in the target area.

In some embodiments, advancing the distal tip of the hollow needle comprises advancing the distal tip of the hollow needle from the gastrointestinal tract location into the target area while the ultrasound transducer is activated.

In some embodiments, the target area is in a liver of the patient.

In some embodiments, the target area in the liver is defined relative to a portal vein of the patient.

In some embodiments, the target area is in or on a gallbladder of the patient.

In a sixth embodiment, a method of electrically coupling a stimulation device to a stimulation member is performed. The method includes: implanting a lead of the stimulation member in a target area within a patient; and coupling a stimulation device connector of the stimulation device to a stimulation member connector of the stimulation member, wherein stimulation generation circuitry of the stimulation device is electrically coupled to the lead of the stimulation member when the stimulation device connector is coupled to the stimulation member connector.

In some embodiments, the method further includes: delivering the stimulation device to a location in a gastrointestinal tract of the patient with the stimulation device connector uncoupled with the stimulation member connector, wherein coupling the stimulation device connector to the stimulation member connector comprises coupling the stimulation device connector to the stimulation member connector at the gastrointestinal tract location.

In some embodiments, coupling the stimulation device connector to the stimulation member comprises coupling the stimulation device connector to the stimulation member connector outside of the patient, and the method further includes: delivering the stimulation device to a location in a gastrointestinal tract of the patient with the stimulation device connector coupled to the stimulation member connector.

In some embodiments, the stimulation member includes a coupling wire that couples the lead to the stimulation member connector, and the method further includes: recoiling, with a recoil device, an access portion of the coupling wire as the stimulation device is delivered to the gastrointestinal tract location.

In some embodiments, the method further includes: delivering the stimulation device to a location in a gastrointestinal tract of the patient by moving the stimulation device over a wire guide.

In some embodiments, coupling the stimulation device connector to the stimulation member connector comprises magnetically coupling the stimulation device connector to the stimulation member connector.

In some embodiments, coupling the stimulation device connector to the stimulation member connector comprises mechanically coupling the stimulation device connector to the stimulation member connector.

In some embodiments, the method further comprises: forming a removable connection between the stimulation device connector and the stimulation member connector when coupling the stimulation device connector to the stimulation member connector.

Other embodiments are possible, and each of the embodiments can be used alone or together in combination. Various embodiments will now be described with reference to the attached drawings.

BRIEF DESCRIPTION OF THE DRAWINGS

FIG. 2 shows a perspective view of a distal portion of the endoscopic ultrasound medical device of FIG. 1.

FIG. 3 shows a side view of the distal portion of the endoscopic ultrasound device moved to a predetermined location of a patient's gastrointestinal tract in order to locate a target area of the patient's liver.

FIG. 8A shows a side view of connectors of the electronic stimulation device and the proximal connectors being coupled magnetically.

FIG. 8B shows a side view of connectors of the electronic stimulation device and the proximal connectors being coupled using conductive hook and fastener material.

FIG. 8C shows a side view of connectors of the electronic stimulation device and the proximal connectors being coupled by forming a press fit connection.

DETAILED DESCRIPTION

Figure 1:
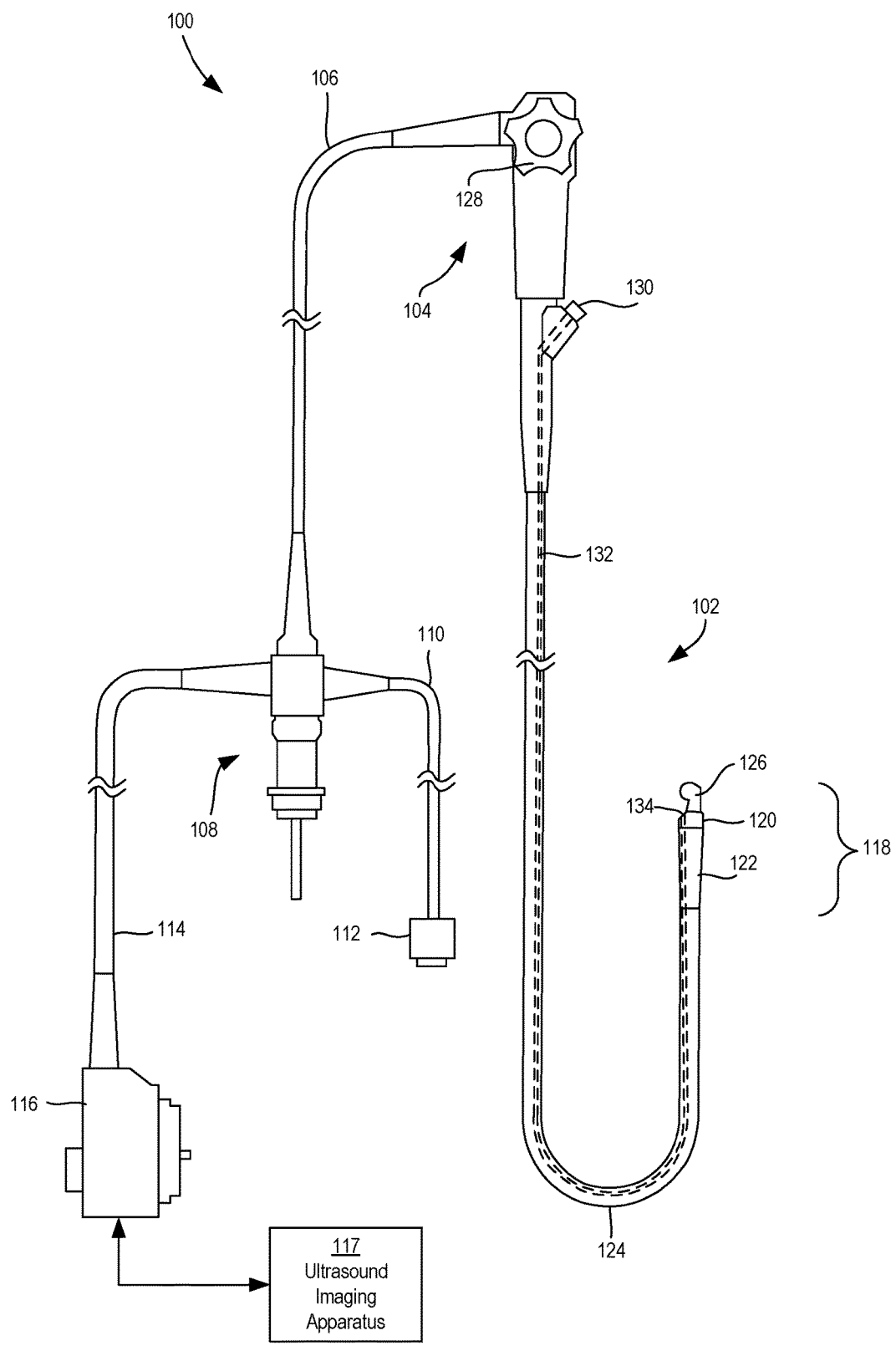
FIG. 1 shows a schematic diagram of an endoscopic ultrasound medical device.

The present description describes electrotherapeutic medical devices, systems, and methods for: (1) stimulating a patient's hepatic branch of the vagus nerve, (2) positioning stimulation electrodes or leads using endoscopic ultrasound, and (3) coupling a stimulation device to stimulation leads inside a patient using magnetic connectors. Various embodiments of these three electrotherapeutic features may be used alone or together in combination.

The vagus nerve is a cranial nerve that originates in the brain, as opposed to the spinal cord. The vagus nerve innervates the cranium, face, and neck, as well as other portions of the body, including internal organs of the chest and abdomen, and is divided into four divisions: cranial, cervical, thoracic, and abdominal. The abdominal division in particular has various branches, including the gastric, hepatic, pyloric, adrenal, and intestinal branches. The hepatic branch extends into the liver. Electrical stimulation of the hepatic branch may be a form of electrical stimulation therapy used for pain management, glucose metabolism regulation, and/or for treatment of any of a variety of health disorders, including but not-limited to obesity, gastroparesis, diabetes, hypertension, and cholecystitis. Specifically targeting the hepatic branch for electrical stimulation rather than the liver generally may improve the effects that electrotherapy may have on some or all of these.

In order to stimulate the hepatic branch, electrically conductive leads may be positioned within a target area of a patient's liver that is sufficiently close to the hepatic branch. Once the leads are positioned in the target area, they may be electrically activated, which in turn may cause the leads to stimulate the hepatic branch.

The hepatic branch and/or the target area that is sufficiently close to the hepatic branch may not be identified directly. Instead, in order to locate the target area, the patient's hepatic portal vein (or simply portal vein) may be identified. The portal vein is a blood vessel that conducts blood carrying nutrients from the GI tract and spleen to the liver. The liver processes the nutrients and also filters toxins that may have been ingested with food. In the liver, at least some portions of the hepatic branch and the portal main may be relatively near or extend in parallel with each other. Due to their close proximity to each other, directly locating the portal vein may be a way of indirectly locating the hepatic branch. Once the portal vein is identified, a target area located near, adjacent, or around the portal vein for positioning the leads to stimulate the hepatic branch may be determined. Since the hepatic branch is near the portal vein, then that target area may be sufficiently close to the hepatic branch for electrical stimulation of the hepatic branch. Specifically positioning the leads in a targeted area inside the liver relative to the portal vein and/or hepatic branch, as opposed positioning the leads on a surface of the liver in order to perform electrotherapy on the liver generally, may improve the beneficial effects that electrotherapy may have on a variety of health related issues identified above, including pain management, glucose metabolism regulation, and various health disorders.

The portal vein and/or the target area near the portal vein may be identified or located in various ways and/or using various medical techniques. One way is through fluoroscopy, during which a contrast agent may be injected into the patient's venous system and X-rays be transmitted through the body, including the portal vein with the contrast agent passing through it, which in turn may generate an image of the portal vein. Another way of identifying the portal vein may be through invasive surgery, during which an incision may be made to gain access into the patient's abdominal cavity. The portal vein may be then identified using direct visualization techniques.

Another way that the portal vein and/or the target area relative to the portal vein may be identified or located is by using ultrasound due to the portal vein's blood-carrying or blood-flow characteristics. In one example type procedure, an endoscope may be used in conjunction with the ultrasound to identify the target area. In particular, an endoscope may be inserted into the patient's gastrointestinal (GI) tract and its distal end may be moved to a predetermined location in the GI tract near the liver and/or where the liver may be accessible from the GI tract. Example predetermined locations of the GI tract may be the stomach and the duodenum, although other locations may be possible. A distal end of the endoscope may reach the predetermined location of the GI tract by being inserted into the patient's mouth and moved through the esophagus to the stomach, and possibly further to the duodenum.

FIG. 1 shows a schematic diagram of an endoscopic ultrasound medical device 100 that may be used to identify at least a portion of the portal vein of a patient and a target area of the liver relative to the portal vein portion. The endoscopic ultrasound device 100 may include an elongate insertion portion 102, an operation portion 104 operatively coupled to a proximal end of the elongate insertion portion 102, and a first electrical cable 106 connected or coupled to the operation portion 104. The first electrical cable 106 may terminate with a first connector 108, which may be configured to be connected to a light source (not shown). Additionally, a second electrical cable 110 may be coupled to the first connector 108 and terminate with a second connector 112, which may be configured to be connected to a camera control unit (not shown). An ultrasound cable 114 may also be coupled to the first connector 108 and may terminate with an ultrasound connector 116, which may be configured to be connected to an ultrasound observation apparatus 117. As described in further detail below, the ultrasound observation apparatus 117 may be configured to generate and display ultrasound images based on ultrasound transmitted and received by the an ultrasound transducer 126.

The elongate insertion portion 102 may be configured for insertion into a patient, such as into and movable through the GI tract of a patient. A distal portion 118 of the elongate insertion portion 102 may include a rigid distal end portion 120 and a bending portion 122. A proximal end of the bending portion may be coupled to an elongate, flexible tubular member 124 of the elongate insertion portion 102. In addition, the ultrasound transducer 126 configured to transmit and receive ultrasound may be coupled to the rigid distal end portion 120.

The operation portion 104 may include an angle knob 128 that controls the bending of the bending portion 122. The operation portion 104 may also include an insertion port or opening 130 in fluid communication with a working or accessory channel or lumen 132 longitudinally extending in the elongate tubular member 124. As shown in FIG. 1, the working channel 132 may longitudinally extend from the insertion port 130 to a distal opening 134 disposed at the rigid distal end portion 120. As described in further detail below, the working channel 132 may be used to deliver a distal portion of a lead insertion device to a treatment site within a patient for insertion of one or more leads into a target area of the liver.

FIG. 2 shows a perspective view of the distal portion 118 of the elongate insertion 102 in more detail. FIG. 2 shows the ultrasound transducer 126, the bending portion 122, the rigid distal end 120, and the distal opening 134 of the working channel 132. FIG. 2 also shows a light source 136 configured to illuminate a treatment area and an optical lens 138 configured to capture and focus light in order to generate images based on the captured and focused light. The light source 136 and the lens 138 may be components of the endoscope's camera system.

FIG. 3 shows a side view of the distal portion 118 of the endoscopic ultrasound device 100 moved to a predetermined location 302 within a patient's GI tract, which may be determined to be a desired location for accessing a portion 304 of the patient's liver from the GI tract. As shown in FIG. 3, the GI tract location 302 and the liver portion 304 may be separated by an anatomical boundary 306, which may include the GI wall as well as any other biological matter separating the GI tract location 302 and the liver portion 304, such as the lesser omentum for example. The endoscope's 100 camera system, including the light source 136 and/or the lens 138 shown in FIG. 2, may be used to guide the distal portion 118 to the GI tract location 302.

A method of identifying a target area in which to place leads for stimulation of the patient's hepatic branch is described with reference to FIG. 3. When the distal portion 118 is at the GI tract location 302, the ultrasound transducer 126 may be activated. Upon activation, the ultrasound transducer 126 may transmit and receive ultrasound. The transmitted ultrasound may extend beyond the GI tract location 302 to the liver portion 304. Based on the transmitted and received ultrasound, a portion of the portal vein 308 in the liver portion 304 may be located. In particular, the ultrasound imaging apparatus 117 (FIG. 1) may receive information about the transmitted and received ultrasound and use ultrasound-based diagnostic imaging techniques to the ultrasound information to generate images, which may indicate the portal vein portion 308. Although not shown in the ultrasound images, a portion of the patient's hepatic branch 310 may be located sufficiently close or adjacent to the portal vein portion 308 identified from the ultrasound imaging. Based on the ultrasound imaging, a target area 312 defined by the portal vein portion 310 indicated in the ultrasound image, denoted in FIG. 3 by the dotted lines, may be determined for positioning stimulation leads. The target area 312 may be determined to be sufficiently close to the portal vein portion 308 such that activation of the leads will stimulate the nearby hepatic branch portion 310. In one example, the boundary of the target area 312 may defined by a distance of ten millimeters from the portal vein portion 308. In addition or alternatively, the target area 312 may be area to be occupied by a lead of a stimulation member when implanted in the liver, where when the lead is implanted a distance from lead to the portal vein portion 308 is within ten millimeters.

After the target area 312 is determined, one or more leads of one or more stimulation members may be positioned or implanted in the target area 312. Leads may be implanted in various ways. In one example, the leads may be delivered to the GI tract location 302 and implanted into the target area 312 endoscopically.

Figure 4:
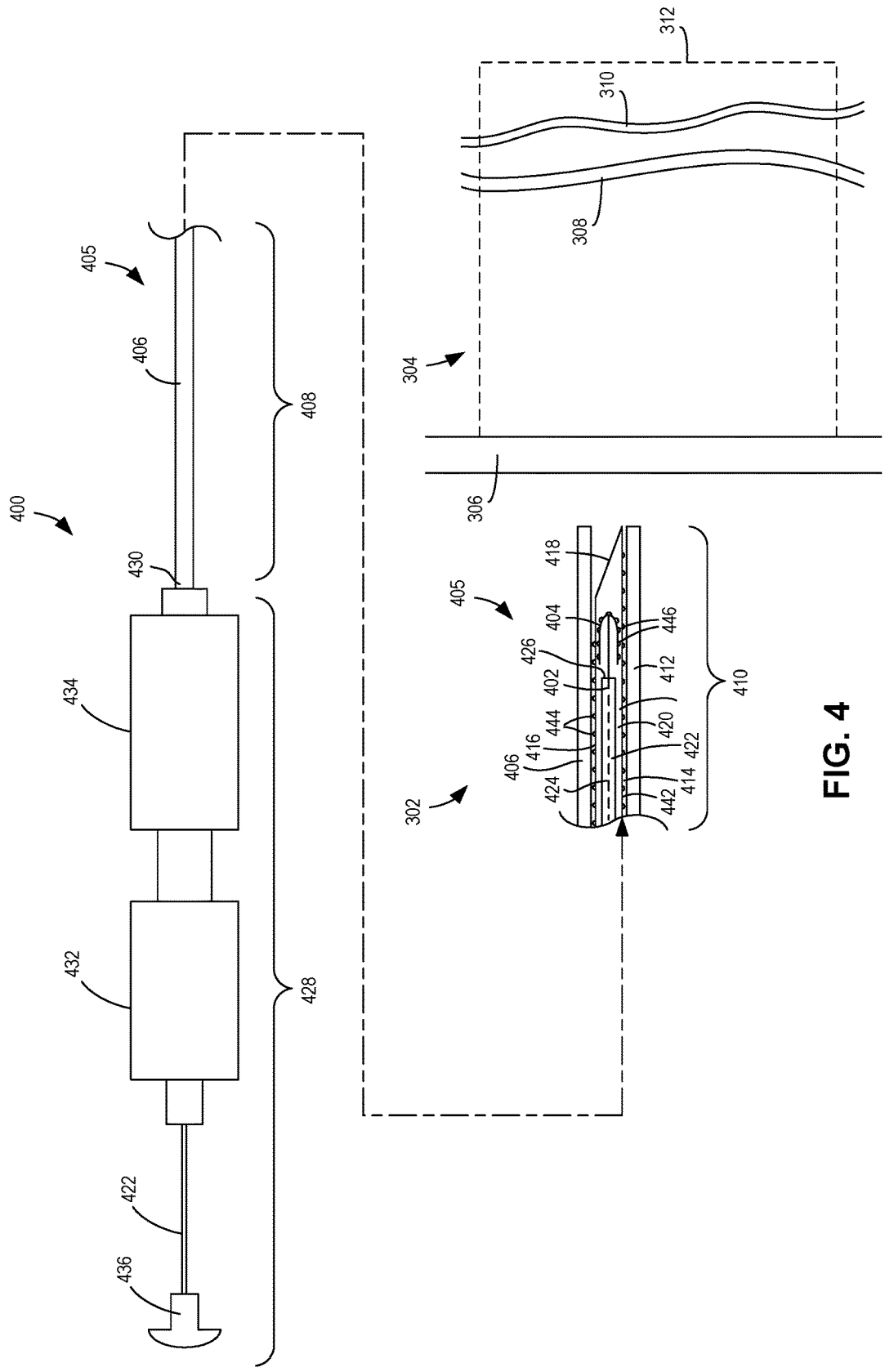
FIG. 4 shows a side view of a stimulation member delivery and deployment device, with a distal portion of the delivery device moved to a location of the gastrointestinal tract.

FIG. 4 shows a side view of an example stimulation member delivery and deployment device 400 configured to deliver a stimulation member 402 to the GI tract location 302 and position a distal, conductive lead 404 of the stimulation member 402 within the identified target area 312. The delivery and deployment device 400 may include an elongate insertion portion 405 that extends from a proximal portion 408 to a distal portion 410. The elongate insertion portion 405 may include an elongate tubular member 406, such as a catheter, that longitudinally extends from the proximal portion 408 to the distal portion 410. The elongate tubular member 406 may include a body 412 and a lumen 414 longitudinally extending in the body 412 from the proximal portion 408 to the distal portion 410. A hollow needle 416 may longitudinally extend and be movably disposed within the lumen 414. The needle 416 may have a sharp and/or beveled distal tip 418 that is capable of puncturing the anatomical boundary 306.

The stimulation member 402 may be disposed and/or loaded within a needle lumen 420 of the hollow needle 416. An elongate deployment member 422, such as a stylet or an inner catheter, may also be movably disposed in the needle lumen 420, longitudinally extending from the proximal portion 408 to the distal portion 410. The deployment member 422 may be configured to engage with the stimulation member 402 to move the lead 404 from within the needle lumen 420 to the target area 312. In addition to the lead 404, the stimulation member 402 may include a coupling wire or other elongate conductive member 424 that electrically couples the lead 404 to a stimulation device (not shown in FIG. 4). Where the elongate deployment 422 is an inner catheter, the coupling wire 424 may longitudinally extend within a lumen of the inner catheter. Alternatively, where the elongate deployment member 422 is a stylet (or other solid elongate member), the elongate deployment member 422 may be disposed adjacent the coupling wire 424. In either case, and as described in further detail below, a distal end 426 of the elongate deployment member 422 may engage with the lead 404 and distally advance the lead 404 in order to deploy it in the target area 312.

The tubular member 406, the needle 416, and the deployment member 422 may be configured to longitudinally move relative to each other. To enable the relative movement, the tubular member 406, the needle 416, and the deployment member 422 may each be operatively coupled to a handle assembly 428, which may be connected to a proximal end 430 of the elongate insertion portion 406. In the example configuration, the handle assembly 428 may include a first portion 432 and a second portion 434 that may be configured to longitudinally move relative to each other. One of the first portion and the second portion 432, 434 may be operatively coupled to the elongate tubular member 406 and the other of the first and second portions 432, 434 may be operatively coupled to the needle 416. To longitudinally move the needle 416 relative to the tubular member 406, the first and second portions 432, 434 may be longitudinally moved relative to each other in a corresponding manner. Additionally, as shown in FIG. 4, a proximal portion of the elongate deployment member 422 may extend through the first and second portions 432, 434, and a proximal end of the elongate deployment member 422 may be coupled to a proximal end cap 436, which may facilitate with operation (e.g. longitudinal movement) of the elongate deployment member 422. The proximal end cap 436 may be used to move the proximal portion of the elongate deployment member 422 relative to the first and second portions 432, 434 of the handle assembly in order to move the deployment member 422 relative to the tubular member 406 and the needle 416. Other configurations of the handle assembly 428 may be possible.

A method of positioning implanting the conductive lead 404 in the target area 312 using the stimulation member delivery and deployment device 400 is described with reference to FIGS. 4-6. Referring particularly to FIG. 4, in some example methods, the distal portion 410 of the elongate insertion portion 405 may be delivered to the GI tract location 302 endoscopically, such as by advancing the elongate insertion portion 405 through a working channel of an endoscope.

Figure 5:
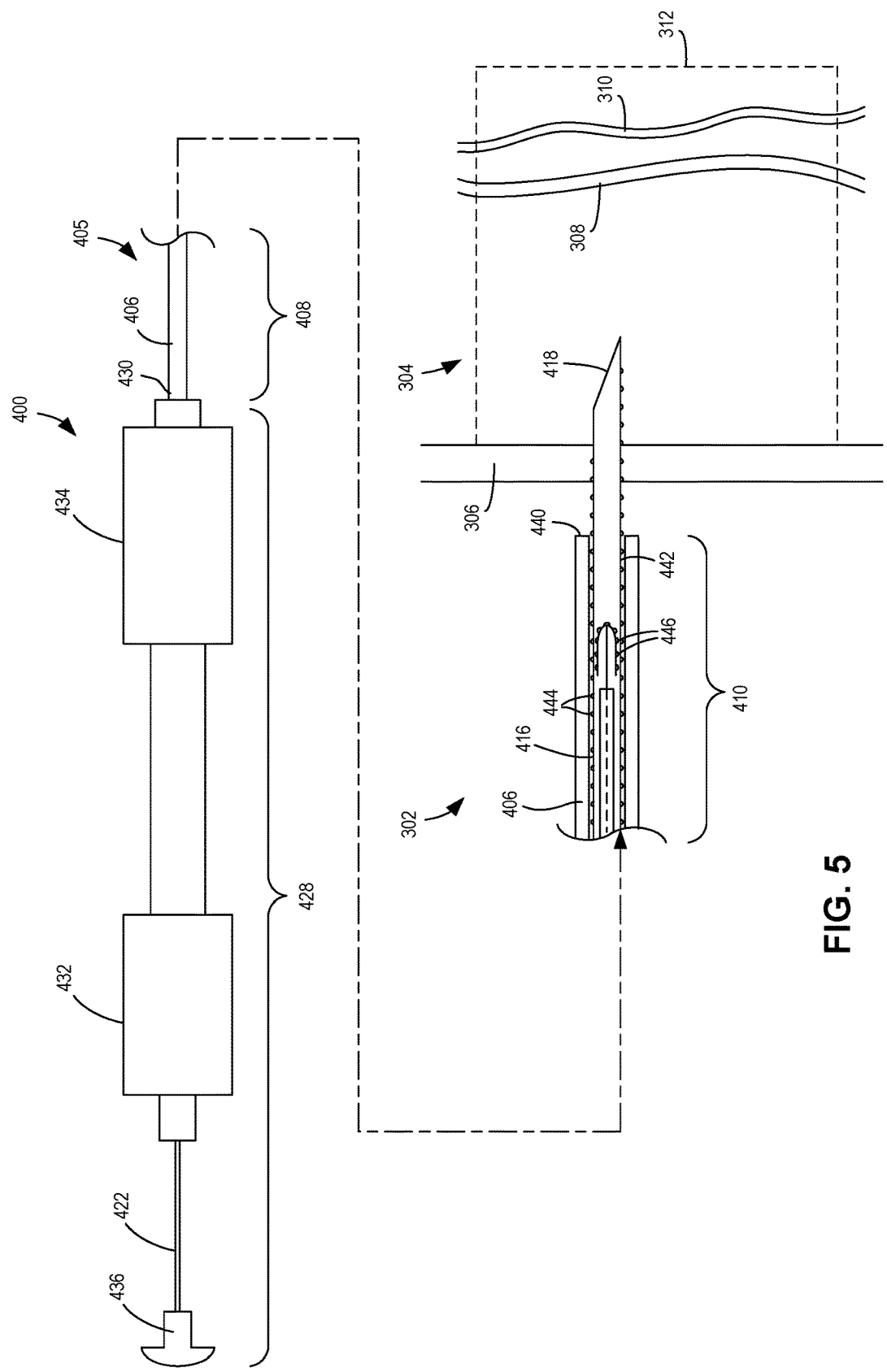
FIG. 5 shows a side view of the stimulation member delivery and deployment device of FIG. 4, with a needle being inserted into a target area.

Referring to FIG. 5, once the distal portion 410 is at the GI tract location 302, the needle 416 may be distally advanced so that its distal tip 418 punctures the anatomical wall 306 and gains access into the liver portion 304. Referring to FIG. 6, the deployment member 422 may then distally advance the lead 404 into the target area 312, where the lead 404 may be securely maintained. FIG. 5 shows the distal tip 418 of the needle 416 being distally advanced past a distal end 440 of the elongate tubular member 406, puncturing the anatomical boundary 306, and entering the target area 312 of the liver portion 304. FIG. 6 shows the deployment member 422 engaging with the stimulation member 402 and having distally advanced or pushed the lead 404 through the needle lumen 420 and past the distal tip 418 of the needle 416 into the target area 312.

For other example positioning or deployment methods, the needle 416 may not be used to first puncture the anatomical wall 306. Instead, the lead 404 itself may be sufficiently sharp or beveled to puncture the wall 306 and be deployed in the target area 312 without the assistance of the distal tip 418 of the needle 416. To perform these methods, the needle 416 may not be included as part of the stimulation member delivery and deployment device 400, or at least may not be used. The distal end of the elongate tubular member 406 may be delivered sufficiently close to the anatomical wall 306, and the deployment member 422 may then engage with the lead 404 and push the lead 404 through the wall 306 and into the target area 312 of the liver portion 304. The deployment member 422 may then be retracted, leaving the lead 404 in the target area.

Figure 6:
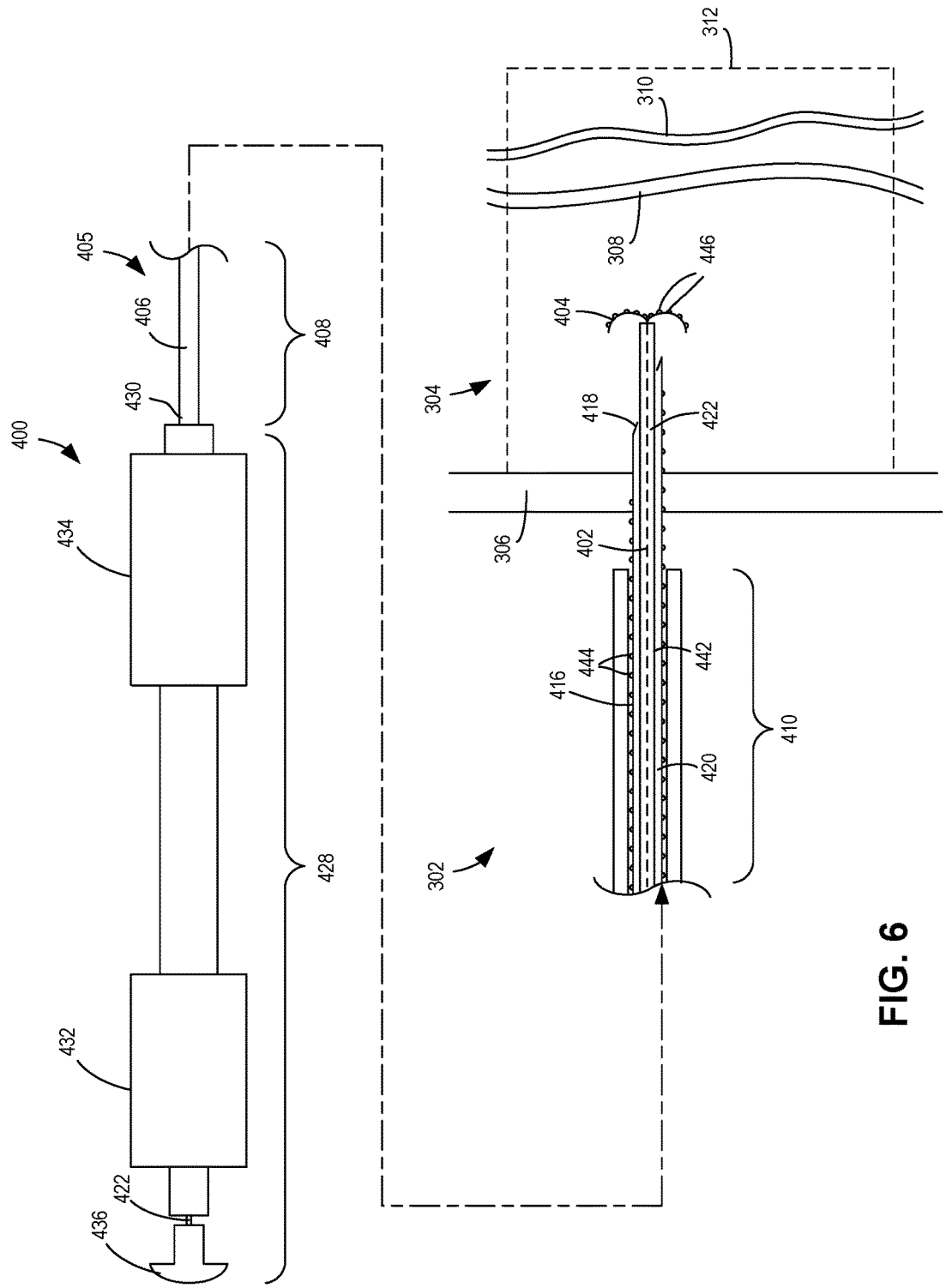
FIG. 6 shows a side view of the stimulation member delivery and deployment device of FIGS. 4 and 5, with a lead being inserted into the target area.

Referring to any of FIGS. 4-6, the lead 404 may be made of a conductive material so that it may be electrically activated. An example material is nitinol, although other conductive materials are possible. Additionally, for some example configurations, such as the configuration shown in FIGS. 4-6, the lead 404 may be configured as an anchor and/or have one or more irreversible barbs that spring outward once it exits and/or is unbiased or unencumbered by the needle lumen 420. This way, the lead 404 may be securely maintained in the target area 312 once it is deployed.

For some examples, the above method of positioning the lead 404 in the target area 312 may be performed under the guidance of ultrasound. For example, the elongate insertion portion 405 may be advanced through the working channel 132 of the endoscopic ultrasound device 100 in order to move the distal portion 410 to the GI tract location 302. The ultrasound transducer 126 may also be positioned in the GI tract location 302, such as what is shown in FIG. 3. When activated, the ultrasound transducer 126 may transmit ultrasound, which may be used to generate images, including real-time images, of the needle 416 and/or the stimulation member 402 being distally advanced into and/or implanted in the target area 312. For some example configurations, one or both of an outer surface 442 of the needle 416 and/or the lead 404 may include one or more dimples 444, 446, which may enhance the ultrasound visibility of the needle 416 and/or the lead 404. FIGS. 4-6 show both the needle 416 and the lead 404 including dimples 444, 446, although in other configurations, only one of the needle 416 or the lead 404, or alternatively both the needle 416 and the lead 404, may not include dimples.

Where ultrasound is used to both identify the target area 312 and guide the deployment and positioning of the lead 404 in the target area 312, the methods may be performed in a continuous operation. For example, the ultrasound transducer 126 may be delivered to the GI tract location 302, and the portal vein portion 308 and corresponding target area 312 may be identified using ultrasound imaging. Subsequently, while leaving the distal portion 118 of the endoscopic ultrasound device 100 at the GI tract location 302, the elongate insertion portion 405 may be advanced through the working channel 132 until the distal portion 410 is at the GI tract location 302. The ultrasound transducer 126 may remain activated or be re-activated in order for the physician to observe the needle 416 and/or the lead 404 being distally advanced into the target area 312 via ultrasound imaging.

Figure 7:
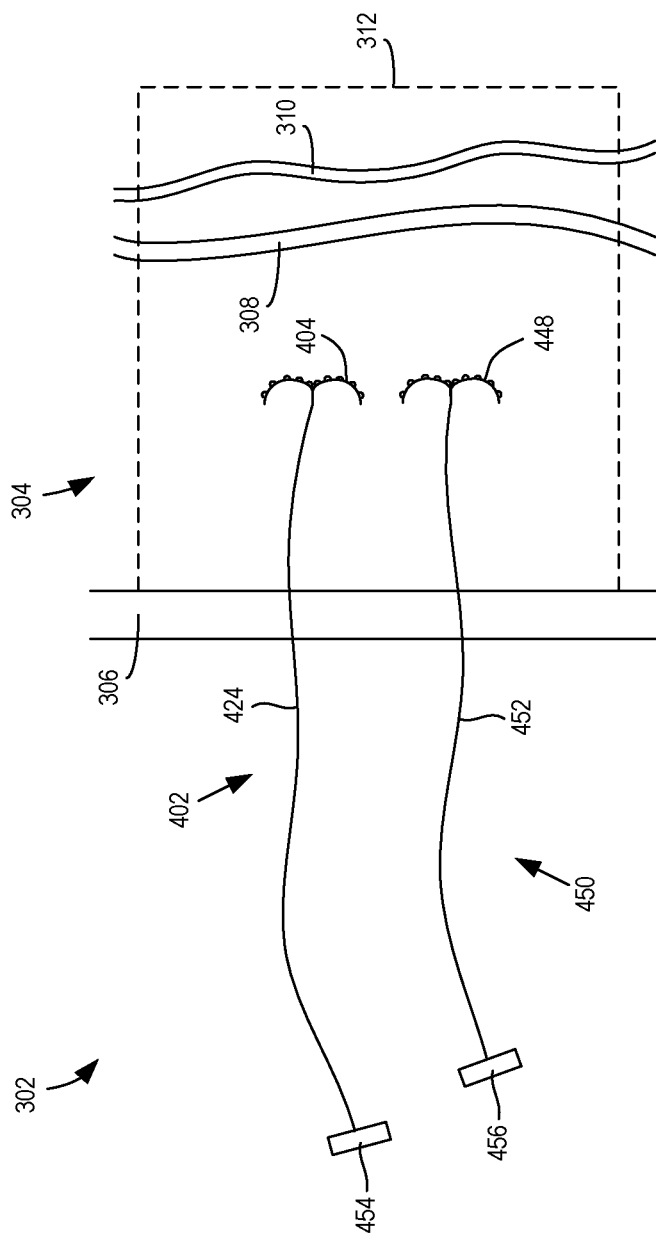
FIG. 7 shows a side view of a pair of stimulation members being deployed, with the leads positioned in the target area and proximal connectors disposed in the gastrointestinal tract location.

Referring to FIG. 7, more than one lead 404 may be deployed in the target area 312. For example, a second lead 448 of a second stimulation member 450 may be deployed in the target area 312 in order to complete an electrical circuit for electrical stimulation. To illustrate, the first lead 404 may be a positive or active lead, and the second lead 448 may be a negative or return lead. In still other deployment methods, more than two leads may be deployed. The number of leads that are deployed may depend on the number of leads to be connected to a stimulation device and/or the number of leads desired to be used to stimulate the hepatic branch portion 310.

The second lead 448 (as well as any further additional leads) may be deployed in a similar way as the first lead 404 is deployed. In some examples, the elongate deployment member 422 may be withdrawn from the patient and loaded with the second stimulation member 450, while the other components of the delivery and deployment device 400 may remain within the patient at the GI tract location 302. In other example methods, the entire delivery and deployment device 400 may be withdrawn from the patient in order to load the second stimulation member 450 into the needle lumen 420. In still other example methods, the entire delivery and deployment device 400 may be withdrawn from the patient and a new or different delivery device may be used to deliver the second stimulation member 450. In still yet other example methods, the second stimulation member 450 may be concurrently disposed in the needle lumen 420 with the first stimulation member 402 and/or no components of the delivery and deployment device 400 may be withdrawn from the patient in order for the second stimulation member 450 to be deployed in the target area 312. Various ways of deploying more than one lead in the target area 312 may be possible.

As shown in FIG. 7, a proximal end of the coupling wire 424 of the first stimulation member 402 and a proximal end of a coupling wire 452 (or other elongate conductive member) of the second stimulation member 450 may each proximally terminate and/or be coupled with a respective connector 454, 456 configured to mate with a corresponding connector of a stimulation device (not shown in FIG. 7) in order for the leads 404, 448 to be electrically coupled to the stimulation device. In the example configuration shown in FIG. 7, lengths of the coupling wires 424, 452 may be such that when the delivery and deployment device 400 is withdrawn from the patient, the connectors 454, 456 are disposed in or near the GI tract location 302, or at least still within the patient.

Figure 8:
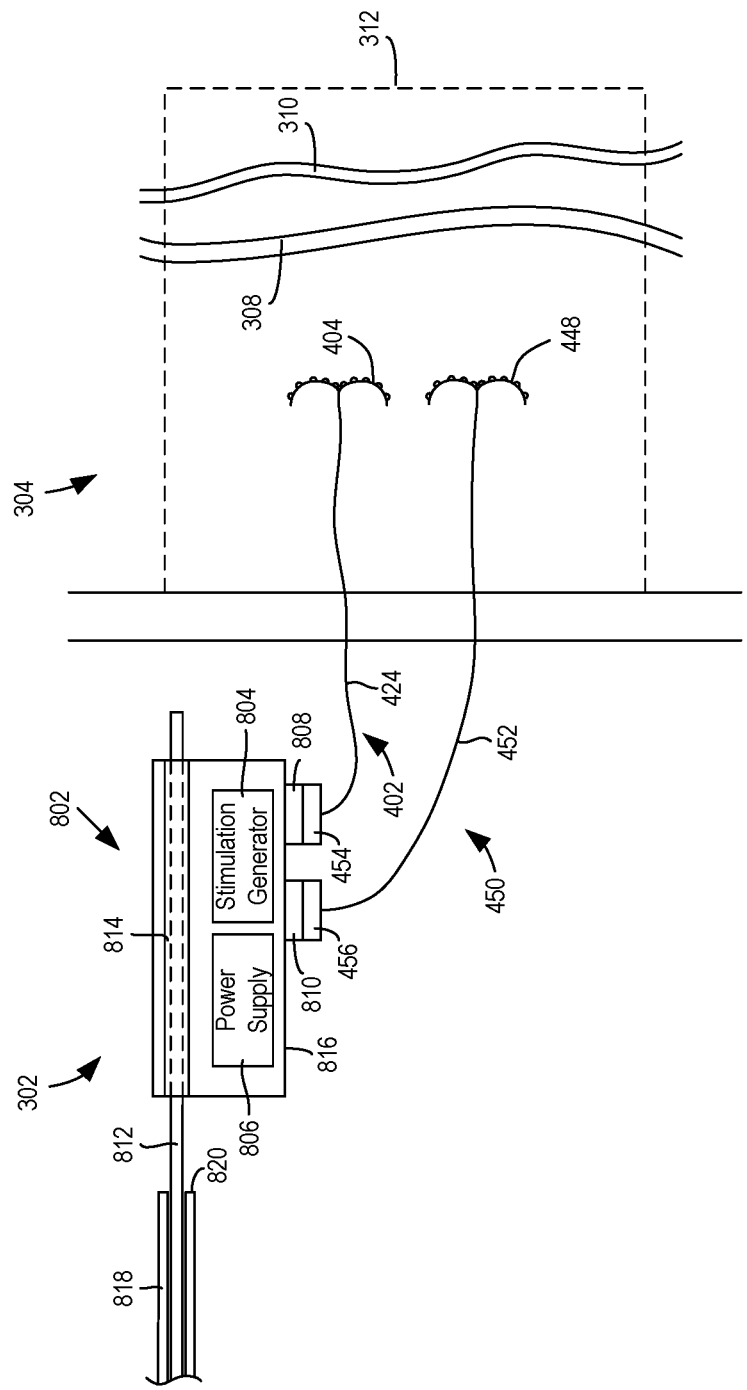
FIG. 8 shows a side view of an electronic stimulation device connected to the proximal connectors of the pair of stimulation members of FIG. 7.
Figure 9:
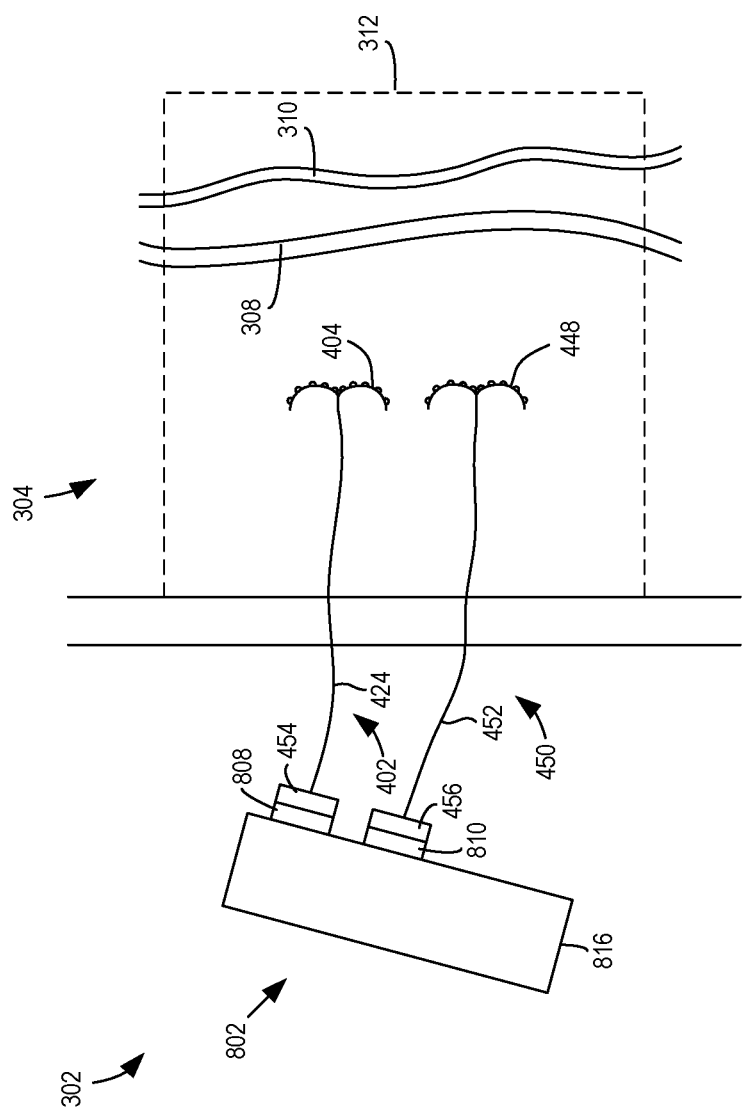
FIG. 9 shows a side view of the electronic stimulation device of FIG. 8 disposed in the gastrointestinal tract location after a wire guide is removed.

Referring to FIGS. 8 and 9, a stimulation device 802 and an associated method of delivering the stimulation device 802 to the GI tract location 302 and electrically coupling the stimulation device 802 to the leads 404, 448 is described. Referring particularly to FIG. 8, with the stimulation member connectors 454, 456 disposed in the GI tract location 302 and the leads 404, 448 disposed in the liver portion 304, the stimulation device 802 may be delivered to the GI tract location 302 to be electrically coupled to the first and second stimulation members 402, 450. The stimulation device 802 may include stimulation generation circuitry 804 configured to generate electrical stimulation signals used to activate the leads 404, 448 and stimulate the hepatic branch portion 310. The electrical stimulation signals may be pulsed signals and/or have a pulsed waveform. The pulsed signals may have a pulse frequency or rate of about 40 Hertz (Hz) or less. In one example, the pulse frequency may be 14 Hz. Additionally, the pulsed signals may have a pulse width of about 0.3 milliseconds (ms). Also, a power component of the pulsed signals may by about 13 Watts (W) or less. In one example, the power is 5 Watts. In addition or alternatively, a current component of the pulsed signal may have a maximum amplitude of 4 milliAmps (mA). In one example, the maximum amplitude of the current component may be 1 mA.

In addition, some example configurations of the stimulation device 802 may include power supply circuitry 806, such as a battery, that is configured to power the stimulation generation circuitry 804 in order for the electrical stimulation signals to be generated. For other example configurations, the power supply circuitry 806 may be an electronic circuit or device other than a battery and/or be configured external to the stimulation device 802. As examples, the stimulation generation circuitry 804 may be powered using energy generated or produced by the patient's body or by magnetic inductance generated from movement of a device, such as one that may be worn by the patient. Any of various power supply circuitry, now or later developed, may be used to power the stimulation generation circuitry 804.

The stimulation device 802 may be delivered to the GI tract location 302 (or wherever else within the patient where the stimulation member connectors 454, 456 are located) in various ways. For some example methods, the stimulation device 802 may be wire guidable, meaning that a wire guide 812 may be used to guide and/or deliver the stimulation device 802 to the GI tract location 302. The stimulation device 802 may include a wire guide engaging portion 814, such as a channel as shown in FIG. 8, that is configured to and/or sized to engage with the wire guide 812 in order for the stimulation device 802 to be movably disposed about the wire guide 812. Configurations for the wire guide engaging portion 814 other than a channel may be possible. For example, the stimulation device 802 may include one or more rings or hollow structures extending from an outer housing 816 of the stimulation device 802.

The wire guide 812 may longitudinally extend from a distal end in the GI tract location 302 to a proximal end outside of the patient, where the wire guide engaging portion 814 may engage with and be disposed about the wire guide 812. The stimulation device 802, initially not coupled with the stimulation members 402, 450, may be distally advanced over the wire guide 812 and delivered to the GI tract location 302. For some example methods, in order to distally advance the stimulation device 802 over the wire guide 812, a catheter or other wire guidable pushing device 818 may be inserted over the wire guide 812 after the stimulation device 802 is positioned about the wire guide 812 so that a distal end 820 of the catheter 818 is proximal the stimulation device 802. To distally advance the stimulation device, the distal end 820 of the catheter 818 may engage with the stimulation device 802. Distal advancement of the catheter 818, then, may distally advance the stimulation device 802 to the GI tract location 302.

Prior to positioning the stimulation device 802 about the wire guide 812, a distal portion of the wire guide 812 may be distally advanced to the GI tract location 302, as shown in FIG. 8. To do so, the wire guide 812 may be inserted into and advanced through the working channel 132 of the endoscopic ultrasound device 100 (or a working channel of a different endoscope if such an endoscope other than the endoscopic ultrasound device 100 is used) until the distal portion of the wire guide 812 is at the GI tract location 302. If the stimulation device 802 is too large to be inserted into and moved within the working channel 132, the elongate insertion portion 102 may be removed from the patient, while the wire guide 812 is kept within the patient. The stimulation device 802 may then be positioned over the wire guide 812 and advanced to the GI tract location 302 after the elongate insertion portion 102 is removed from the patient.

When the stimulation device 802 reaches the GI tract location 302, the stimulation device 802 may be electrically coupled to the stimulation members 402, 450. The stimulation device 802 may further include connectors 808, 810 configured to engage with and/or mate with the connectors 454, 456 of the stimulation members 402, 450. When the stimulation device connectors 808, 810 are mated and/or engaged with the stimulation member connectors 454, 456, the stimulation device 802 may be electrically coupled to the stimulation members 402, 450 and configured to deliver the electrical stimulation signals to the leads 404, 448 implanted in the target area 312.

The stimulation member connectors 454, 456 and the stimulation device connectors 808, 810 may have any of various configurations to mate, engage, physically contact and/or form a removable connection with each other and electrically couple the stimulation device 802 with the stimulation members 402, 450. FIGS. 8A-8C show various exemplary, non-limiting configurations for the connectors 454, 456, 808, 810. In particular, FIG. 8A shows the connectors 454, 456, 808, 810 being configured for magnetic coupling, and FIGS. 8B and 8C show the connectors 454, 456, 808, 810 being configured for various types of mechanical coupling, including a hook-and-loop coupling in FIG. 8B and a press-fit coupling in FIG. 8C.

Referring to FIG. 8A, for some example configurations, at least two of the connectors 454A, 456A, 808A, 810A may be magnetic and appropriately polarized in order to facilitate the connections. In some of these configurations using magnets, all of the connectors 454A, 456A, 808A, 810A may be magnetic. For other configurations, less than all of connectors 454A, 456A, 808A, 810A may be magnetic. Those that are not magnetic may be made of a metallic material that is attracted to magnets. The magnetic connectors may create magnetic fields 870A, 872B that are appropriately polarized in order to attract one of the connectors from the other pair.

Referring to FIG. 8B, for other example configurations, connectors 454B, 456B, 808B, 810B may include conductive hook and loop fastener material (e.g., Velcro®) 874B to mechanically secure stimulation member connector 808B with stimulation device connector 454B and stimulation member connector 810B with stimulation device connector 456B. Example, non-limiting conductive materials for the hook and loop fastener material 874B may include silver, copper, gold, or tungsten.

Referring to FIG. 8C, for other example configurations, connectors 454, 456, 808, 810 may have a press-fit configuration. For example, as shown in FIG. 8D, the stimulation device connectors 808D, 810D may be conductive receptacles, and the stimulation member connectors 454D, 456D may be inserted into and press-fit with the receptacles 808D, 810D. Other press-fit configurations may be possible.

Another example type of mechanical coupling configuration for the stimulation member connectors 454, 456 and stimulation device connectors 808, 810 may be to use clips, such as endoscopic clips (i.e., endoclips), to couple the stimulation member connectors 454, 456 with the stimulation device connectors 808, 810. Various other ways of connecting the stimulation device and member connectors 454, 456, 808, 810 may be possible.

Referring back to FIG. 8, when the stimulation device 802 reaches the GI tract location 302, the first stimulation device connector 808 may connect with the first stimulation member connector 454 and the second stimulation device connector 810 may connect with the second stimulation member connector 456. When the stimulation device connectors 808, 810 are connected with the stimulation member connectors 454, 456, the stimulation device 802 may be electrically coupled to the stimulation members 402, 450. When electrically coupled, the stimulation device 802 may deliver the electrical stimulation signals to the leads 404, 448 implanted in the target area 312.

Referring to FIG. 9, the wire guide 812 may be withdrawn from outside the patient, leaving the stimulation device 802 disposed in the GI tract location 302 and connected to the stimulation members 402, 450. The stimulation device 802 may continue to supply the stimulation signals to the leads 404, 448 until a time when operation of the stimulation of the device 802 stops.

An outer surface of the housing 816 of the stimulation device 802 may be made of and/or coated with a suitable material to withstand an acidic environment in the GI tract location 302. In some examples, the housing 816 may be coated with a silicone-based or a parylene-based coating. Other example materials and/or coatings may be possible.

Figure 10:
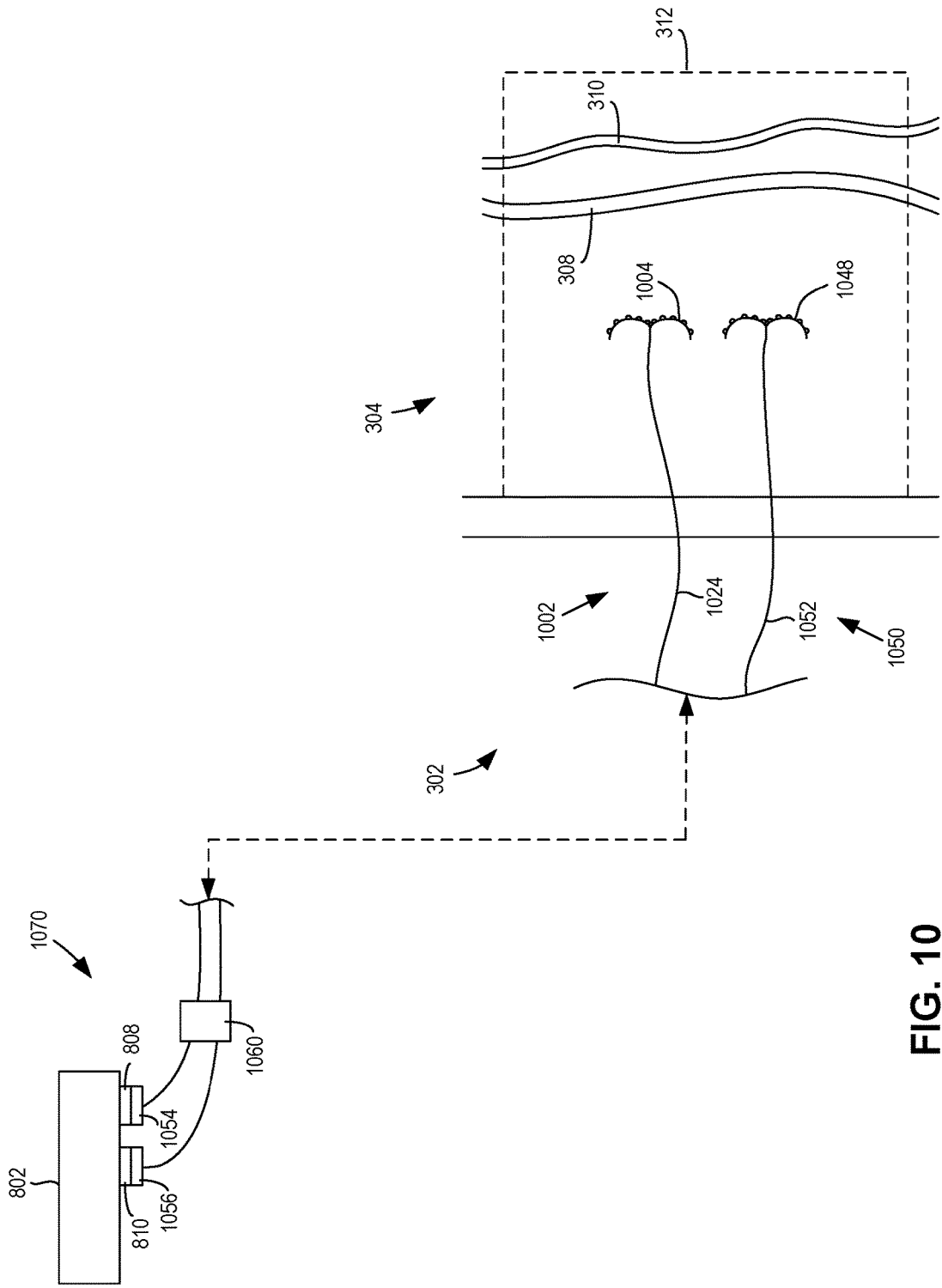
FIG. 10 shows a side view of alternative proximal connectors of stimulation members disposed outside of the patient, where the electronic stimulation device is coupled to the proximal connectors.

FIG. 10 shows alternative stimulation members 1002, 1050, and an alternative method of electrically coupling the stimulation device 802 with the alternative stimulation members 1002, 1050 is described with respect to FIG. 10. Leads 1004, 1048 of the stimulation members 1002, 1050 may be the same as the leads 404, 448 shown and described with respect to FIGS. 4-7. However, coupling wires 1024, 1052 may be longer. As shown in FIG. 10, the lengths of the coupling wires 1024, 1052 may be sufficiently long such that they proximally extend and terminate with stimulation member connectors 1054, 1056 at a location outside the patient rather than inside the patient, such as in the GI tract location 302. The stimulation member connectors 1054, 1056 may remain outside the patient as the leads 1004, 1048 are moved to the GI tract location 302 and then positioned in the target area 312. Since the stimulation member connectors 1054, 1056 are located outside of the patient, the stimulation device connectors 808, 810 of the stimulation device 802 may be initially connected to the stimulation member connectors 1054, 1056 outside of the patient rather than at the GI tract location 302. Any of various ways, including those described with reference to FIGS. 8A-8C, may be used to connect the stimulation device connectors 808, 810 with the stimulation member connectors 1054, 1056. The stimulation device 802, being already coupled to the leads 1004, 1048, may then be delivered to the GI tract 302, such as by being moved over the wire guide 812 as previously described.

In some example configurations, one or more recoil devices 1060 may be implemented with the longer coupling wires 1024, 1052. The recoil device 1060 may recoil or pull in any excess portions of the wires 1024, 1052 in order to compact the area in the GI tract location 302 being taken up by the excess portions. The recoil device 1060 may recoil or pull in the excess portions after the stimulation device 802 is positioned in its final location in the patient, such as the GI tract location 302. Alternatively, the recoil device may continuously recoil or pull in the excess portions as the stimulation device 802 is being distally advanced to the GI tract location 302. FIG. 10 shows the recoil device 1060 external to the housing 816 of the stimulation device 802. In other configurations, the recoil device 1060 may be a component of the stimulation device 802 that withdraws the excess portions to within the housing 818 of the stimulation device 802. Various recoil device configurations may be possible.

FIGS. 4-10 above are described with reference to a target area 312 defined by a portion of a patient's portal vein 308 in the liver. However, the delivery and deployment device 400, with or without the use of endoscopic ultrasound device 100, may be used to endoscopically deploy and implant one or more stimulation member in target areas other than in the liver or areas of the liver other than those determined relative to the portal vein. In general, the distal portion 410 of the elongate insertion portion 405 may be endoscopically delivered to a location within the GI tract of a patient and the components of the delivery and deployment device 400 may be used to deploy and implant, with or without ultrasound guidance, one or more leads of one or more stimulation members in or on an anatomical target area of the patient that is accessible via the GI tract. Another target area besides the liver may be an area in or on the gall bladder. Other target areas accessible from the GI tract may be possible. Similarly, the stimulation device 802 may be delivered to within the GI tract and connected to stimulation members that have leads implanted in or on areas other than a target area of the liver defined relative to the portal vein.

In sum, the endoscopic ultrasound device, the delivery and deployment device 400, and the stimulation device 802 may be used, separately or in combination with one another, to electrically stimulate areas of a patient other than an area within the patient's liver that is defined by an identified portion of the portal vein. Additionally, a target area within a patient's liver defined by the portal vein for purposes of stimulating the hepatic branch of the vagus nerve may be identified using a methodology other than ultrasound, may be implanted with one or more stimulation members using a medical device other than the delivery and deployment device 400, and/or stimulation members implanted in the target area may be stimulated using stimulation devices other than the stimulation device 802.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A method of stimulation, the method comprising:
endoscopically delivering a distal portion of a delivery and deployment device to a location of a gastrointestinal tract of a patient;
with the delivery and deployment device, distally advancing a lead of a stimulation member from the gastrointestinal tract location to a target area within the patient, wherein the lead is implanted in the target area after being moved to the target area;
activating an ultrasound transducer to generate an ultrasound image of at least one of the lead being moved from the gastrointestinal tract location to the target area or the lead implanted in the target area;
coupling a stimulation device connector of a stimulation device to a stimulation member connector of the stimulation member outside of the patient, wherein stimulation generation circuitry of the stimulation device is electrically coupled to the lead of the stimulation member when the stimulation device connector is coupled to the stimulation member connector, and wherein the stimulation member comprises a coupling wire that couples the lead to the stimulation member connector;
delivering the stimulation device to the location in the gastrointestinal tract of the patient with the stimulation device connector coupled to the stimulation member connector; and
recoiling, with a recoil device, an excess portion of the coupling wire.

2. The method of claim 1, further comprising:
advancing a distal tip of a hollow needle of the delivery and deployment device from the gastrointestinal tract location into the target area,
wherein distally advancing the lead of the stimulation member comprises distally advancing the lead from within a needle lumen of the hollow needle past the distal tip of the needle when the distal tip is positioned in the target area.

3. The method of claim 2, wherein advancing the distal tip of the hollow needle comprises advancing the distal tip of the hollow needle from the gastrointestinal tract location into the target area while the ultrasound transducer is activated.

4. The method of claim 1, wherein the ultrasound transducer is coupled to a distal portion of an endoscopic ultrasound device, the method further comprising:
advancing the distal portion of the endoscopic ultrasound device to the gastrointestinal tract location,
wherein endoscopically delivering the distal portion of the delivery and deployment device to the gastrointestinal tract location comprises advancing the delivery and deployment device through a working channel of the endoscopic ultrasound device.

5. The method of claim 1, further comprising:
electrically stimulating the target area with the lead of the stimulation member implanted in the target area.

6. The method of claim 5, wherein the target area is in a liver of the patient, and wherein electrically stimulating the target area comprises electrically stimulating a portion of a nerve in the liver.

7. The method of claim 6, wherein the portion of the nerve comprises a hepatic branch of a vagus nerve.

8. The method of claim 7, wherein the target area in the liver is defined relative to a portal vein in the liver of the patient, wherein the method further comprises transmitting, with the ultrasound transducer, ultrasound toward the portal vein to generate the ultrasound image.

9. The method of claim 7, wherein electrically stimulating the hepatic branch comprises electrically stimulating the hepatic branch with pulsed electrical stimulation signals.

10. The method of claim 9, wherein the pulsed signals have at least one of: a pulse frequency of 40 Hertz (Hz) or less, a pulse width of 0.3 milliseconds (ms), a power component of 13 Watts or less, or a maximum amplitude of a current component of 4 milliAmps (mA) or less.

11. The method of claim 1, wherein the target area is in or on a gallbladder of the patient.

12. The method of claim 1, wherein coupling the stimulation device connector to the stimulation member connector comprises magnetically coupling the stimulation device connector to the stimulation member connector.

13. The method of claim 1, wherein coupling the stimulation device connector to the stimulation member connector comprises mechanically coupling the stimulation device connector to the stimulation member connector.

14. The method of claim 1, wherein recoiling the excess portion of the coupling wire comprises
recoiling, with the recoil device, the excess portion of the coupling wire as the stimulation device is delivered to the gastrointestinal tract location.

15. The method of claim 1, further comprising:
delivering the stimulation device to a location in a gastrointestinal tract of the patient by moving the stimulation device over a wire guide.

16. The method of claim 1, further comprising:
forming a removable connection between the stimulation device connector and the stimulation member connector when coupling the stimulation device connector to the stimulation member connector.

* * * * *